United States Patent [19]

Roizman

[11] Patent Number: 4,859,587
[45] Date of Patent: Aug. 22, 1989

[54] RECOMBINANT HERPES SIMPLEX VIRUSES, VACCINES AND METHODS

[75] Inventor: Bernard Roizman, Chicago, Ill.

[73] Assignee: Institut Merieux, Bains, France

[21] Appl. No.: 856,052

[22] Filed: Apr. 25, 1986

Related U.S. Application Data

[63] Continuation-in-part of Ser. No. 616,930, Jun. 4, 1984.

[51] Int. Cl.[4] .................. C12P 21/00; C12N 15/00; C12N 7/00; A61K 39/00
[52] U.S. Cl. .......................... 435/68; 435/70; 435/91; 435/235; 435/172.3; 435/317.1; 435/320; 935/32; 935/34; 935/57; 935/65; 424/89; 424/85.8; 536/27
[58] Field of Search ............. 435/68, 70, 91, 235, 435/240, 243, 172.3, 317, 240.1, 320; 935/32, 34, 57, 65; 424/85, 89; 536/27

[56] References Cited

U.S. PATENT DOCUMENTS

| | | | |
|---|---|---|---|
| 4,554,159 | 11/1985 | Roizman et al. | 424/89 |
| 4,569,840 | 2/1986 | Kit | 424/89 |
| 4,603,112 | 7/1986 | Paoletti et al. | 435/235 |
| 4,769,331 | 9/1988 | Roizman et al. | 435/172.3 |

FOREIGN PATENT DOCUMENTS

| | | |
|---|---|---|
| 0074808 | 3/1983 | European Pat. Off. . |
| 141458 | 5/1985 | European Pat. Off. . |
| 176170 | 4/1986 | European Pat. Off. . |

OTHER PUBLICATIONS

Post et al. (1981), Cell 24: 555-65.
Mocarski et al. (1980), Cell 22: 243-55.
Roizman et al. (1982), 17, Int'l Congress on Herpes Virus of Man and Animal, Develop. Biol. Standard 52: 287-304.
Watson et al. (1984), J. Invest Dermatol., 83 Suppl. 1, 102-11 (CA101(17):145077u).
Barahona et al., Laboratory Animal Science, 26(6), Part II, 1104-1112 (1976).
Centifanto-Fitzgerald, The Role of Viruses in Human Cancer, vol. II, Girald et al., eds, Elsevier Science Publishers, BV. 25-36 (1984).
Hall et al., Vaccine, 4, 138-150 (1986).
Hsuing et al., Reviews of Infectious Diseases, 6(1), 33-50 (1984).
Melendez et al., Laboratory Animal Care, 19(1), 38-45 (1969).
Meignier et al., Vaccines, 87, Cold Spring Harbor Laboratory, Chanock et al., eds., 368-373 (1987).
Scriba, Infection and Immunity, 12(1), 162-165 (1975).
Stanberry et al., J. Infection Disease, 146(3), 397-404 (1982).
Centifanto-Fitzgerald et al, J. Exp. Med., vol. 155, pp. 475-489 (1982).
Chang et al, J. Bacteriol, vol. 134 at 1141 (1978).
Hayward et al, Proc. Nat. Acad. Sci., USA, vol. 72, No. 11 at 4243-4247 (1975).
Kousoulas et al., Virology, vol. 135, pp. 379-395 (1984).

(List continued on next page.)

Primary Examiner—Thomas G. Wiseman
Assistant Examiner—S. Seidman
Attorney, Agent, or Firm—Marshall O'Toole, Gerstein, Murray & Bicknell

[57] ABSTRACT

Recombinant herpes viruses useful as effective ingredients in vaccines against both virulent HSV-1 and HSV-2 are disclosed. Methods of preparing the recombinant viruses, vaccines incorporating the viruses, and methods of immunizing a human host by inoculation with the vaccines are also disclosed.

The genomes of the recombinant viruses each comprise a mutant of the HSV-1 genome from which a portion thereof responsible for neurovirulence yet nonessential for growth is deleted. A gene from the HSV-2 genome responsible for coding an immunity-inducing glycoprotein is inserted in the mutant genome between the end points of deletion therein.

51 Claims, 8 Drawing

OTHER PUBLICATIONS

Kristie et al., *Proc. Natl. Acad. Sci.*, USA, vol. 81 at 4065–4069 (1984).

Morse et al, "Anatomy of Herpes Simplex Virus (HSV) DNA:X. Mapping of Viral Genes by Analysis of Polypeptides and Functions Specified by HSV-1×HSV-2 Recombinants", *J. Virol.*, vol. 26, No. 2 at 389–410 (May 1978).

Poffenberger et al, *Proc. Natl. Acad. Sci.*, USA, vol. 80, pp. 2690–2694 (1983).

Poffenberger and Roizman, *J. Virol.*, vol. 53, pp. 587–595 (1985).

Post et al., *Proc. Natl. Acad. Sci.*, USA, vol. 77, No. 7 at 4201–4205 (1980).

Roizman et al., *Virology*, vol. 133, pp. 242–247 (1984).

Wadsworth et al., *J. Virol*, vol. 15, No. 6 at 1487–1497 (1979).

PROTECTION IN MICE : HSV-1(F)/G

FIGURE 12

PROTECTION IN MICE : HSV-1(F)/MGH-10

4,859,587

RECOMBINANT HERPES SIMPLEX VIRUSES, VACCINES AND METHODS

CROSS-REFERENCE TO RELATED APPLICATION

This is a continuation-in-part of copending, commonly assigned application Ser. No. 616,930 filed June 4, 1984 in the name of Bernard Roizman and entitled "Herpes Simplex Virus as a Vector".

STATEMENT OF DEPOSIT

Some viruses and plasmids identified herein by ATCC accession number have been deposited with the American Type Culture Collection, 12301 Parklawn Drive, Rockville, Md. 20852 U.S.A. pursuant to the provisions of the Budapest Treaty on the International Recognition of the Deposit of Microorganisms for the Purposes of Patent Procedure.

Specifically, said cultures were deposited as follows: pRB3410 was deposited under accession number ATCC 53350 on Dec. 10, 1985; pRB3498 was deposited under accession number ATCC 53348 on Dec. 10, 1985; pRB3575 was deposited under accession number ATCC 53349 on Dec. 10, 1985; R7017 was deposited under accession number VR2121 on Dec. 10, 1985; R7020 was deposited under accession number VR2123 on Dec. 10, 1985; I358 was deposited under accession number VR2122 on Dec. 10, 1985; HSV-1(F) was deposited under accession number VR733 on Mar. 14, 1973; HSV-2(G) was deposited under accession number VR734 on Mar. 14, 1973; and R3410 was deposited under accession number VR2124 on Dec. 10, 1985.

BACKGROUND OF THE INVENTION

1. Field of the Invention

This invention relates to recombinant virus strains, live viral vaccines, methods of making the strains and vaccines, and methods of immunizing a host against viruses. More specifically, this invention relates to recombinant herpesvirus strains, live viral vaccines incorporating such strains, methods of making the recombinant strains and vaccines, and methods of immunizing a human host against herpes simplex virus types I and II (designated HSV-1 and HSV-2, respectively) using the vaccines.

2. Description of Related Art

Both distinguishable serotypes of herpes simplex virus (HSV-1 and HSV-2) cause infection and disease ranging from relatively minor fever blisters on lips to severe genital infections and generalized infections of newborns. Herpes simplex has increasingly been recognized as an etiologic agent in human encephalitis.

A stable, nontransforming live viral vaccine, which may or may not establish latent infections, and which is effective against both types of herpes simplex virus has long been sought.

In principle, viruses cause infected cells to produce specific proteins. These interact with each other and with cellular proteins, DNA or RNA to cause viral progeny to be made, to destroy the infected cell and to spread infection to previously noninfected cells. Some of these proteins also stimulate host immune response. HSV-1 and HSV-2 are related immunologically, but most of their proteins carry distinguishing characteristics which allow them to be differentiated. See Morse, et al., "Anatomy of Herpes Simplex Virus (HSV) DNA:X. Mapping of Viral Genes by Analysis of Polypeptides and Functions Specified by HSV-1 × HSV-2 Recombinants", *J. Virol.*, Vol. 26, No. 2 at 389–410 (May 1978), the disclosure of which is incorporated herein by reference.

It is known from the formation of recombinant progeny that proteins of HSV-1 can interact with proteins of HSV-2 to form infectious progeny. It is also known that immunity to HSV infection is determined by host response to several proteins.

A virus strain useful in a vaccine against HSV-1 and HSV-2 should be avirulent, stable (i.e. does not revert to the virulent state), provide demonstrated immunity to massive challenges of wild type strains of both HSV-1 and HSV-2, have low pathogenicity, and should not be capable of transforming host cells. In some cases, it may be desirable for the vaccinal virus to disappear after immunization of a host, but in some cases it may be desirable for the virus to remain in a latent form in the host.

Until now, no effective vaccine against both types of herpes simplex viruses exhibiting the desirable characteristics noted above has been known.

SUMMARY OF THE INVENTION

It is an object of the invention to provide live, recombinant virus strains, and vaccines incorporating such strains, effective against virulent, disease-producing (wild-type) HSV-1 and HSV-2, methods of making the vaccines and methods of immunizing a human host using the vaccines.

According to the invention, recombinant virus strains comprising modified HSV-1 genomes carrying HSV-2 genes are provided. These recombinants fulfill the requirements of strains suitable for immunization against HSV-1 and HSV-2 infections, and can also be used as vectors of foreign genes, although the recombinants need not contain such foreign genes other than certain HSV-2 genes.

Other characteristics and advantages of the invention will be apparent from the following detailed description taken in conjunction with the figures and the appended claims.

BRIEF DESCRIPTION OF THE FIGURES

In the Figures, the following abbreviations apply: E=EcoRI; P=PvuII; H=HindIII; X=XbaI; B=BamHI; Bg=BglII; and S=SacI restriction endonuclease sites. TK=thymidine kinase; gG2=HSV-2 glycoprotein G gene; gD2=HSV-2 glycoprotein D gene. Helicies indicate vector sequences. The "v" symbol represents the location of the polylinker.

DETAILED DESCRIPTION OF THE INVENTION

Preliminary

The following describes the preparation of two exemplary recombinant viruses comprising herpes simplex virus type 1 (HSV-1) genomes carrying herpes simplex virus type 2 (HSV-2) genes. These recombinants, designated herein as R7017 (ATCC VR2121) and R7020 (ATCC VR2123), are designed to fulfill the requirements of strains suitable for immunization against HSV-1 and HSV-2 infections, and can also be used as vectors of foreign genes. The exemplary recombinants, as constructed, do not contain foreign genes other than genes from HSV-2.

The structure of HSV DNA is described in the literature. See Wadsworth, et al, *J. Virol,* Vol. 15, No. 6 at 1487–1497 (1979); Hayward, et al, *Proc. Nat. Acad. Sci. USA,* Vol. 72, No. 11 at 4243–4247 (1975); and Morse et al, *J. Virol, Vol.* 26, No. 2 at 389–410 (1978). The HSV-1 and HSV-2 genomes each consist of two covalently linked components, designated L and S. Each component consists of unique sequences ($U_l$ for the L component, $U_s$ for the S component) flanked by inverted repeats. The inverted repeats of the L components are designated ab and b'a'. The inverted repeats of the S components are designated as a'c' and ca. An additional property of both HSV-1 and HSV-2 DNA is that the L and S components invert relative to each other so as to yield four isomers differing solely in their relative orientation of the 2 components (See Wadsworth et al, 1979; and Hayward et al, 1975, both cited above).

These four isomers have been designated as "prototype" (P); "inversion of S component" ($I_S$); "inversion of L component" ($I_L$); and "inversion of both L and S components" ($I_{SL}$).

As described in Centifanto-Fitzgerald et al, *J. Exp. Med.,* Vol. 155, pp. 475–489 (1982), it has been established that the right terminus of the L component of HSV DNA contains genes whose mutation leads to loss of neurovirulence as well as the ability to cause lesions in the cornea. These genes have been mapped approximately between 0.70 and 0.83, but their exact location was not previously known.

Studies by Poffenberger, et al., *Proc. Natl. Acad. Sci. USA,* Vol. 80, pp. 2690–2694 (1983), and Poffenberger and Roizman, *J. Virol.,* Vol. 53, pp. 587–595 (1985), have established that the internal inverted repeats (b'a'-'a'c') are not essential for the growth of HSV-1 in cell culture. Specifically, a recombinant HSV-1 virus (designated I358, ATCC VR2122) was constructed in which a portion of the unique sequences at the right end of the L component as well as most of the inverted repeats at the junction between the L and S components in the prototype arrangement were replaced by a small DNA sequence derived from the HindIII 0 fragment, normally located in the left end of the L component, and the thymidine kinase (TK) gene. The deletion of approximately 13 Kbp of HSV-1 DNA from the inverted repeats of the L and S components in I358 suggested that this virus, or a derivative of this virus, could potentially serve as a vector of HSV DNA or foreign DNA inasmuch as additional DNA sequences could be inserted without affecting the packaging of the genome.

The recombinant I358 itself is not suitable as a vector primarily because of the duplication of the HindIII 0 sequences. Because the HindIII 0 sequences at the novel junction between the L and S component are direct repeats of the sequences contained in the HindIII 0 fragment at its natural locations, the sequences between the HindIII 0 repeats spontaneously delete, and defective genomes accumulate in infected cells and culture. Potentially the defective genomes could interfere with standard genomes and preclude optimal growth of the virus.

Even if the I358 genome were to be reconstructed so as to remove the HindIII 0 sequences duplicated at the novel L-S component junction, it would not be clear whether the genes responsible for neurovirulence of the virus are deleted. Even if they are deleted, the virus as such would be suitable for immunization against HSV-1 only, and not against HSV-2. To protect against HSV-2 it would be necessary to duplicate at least some of the glycoprotein genes of that virus.

The main immune response to HSV-2 and HSV-1 is directed against surface proteins of the virus. The surface proteins of the virus are viral glycoproteins inserted into the virion envelope and into the plasma membrane of infected cells. Currently at least 6 viral glycoproteins are known to be specified by HSV-1 and HSV-2. These are glycoproteins B, C, and H mapping in the L component and glycoproteins D, E, and G mapping in the S component. Of these glycoprotein genes, those that induce neutralizing antibody and presumably those that induce immunity are glycoprotein D mapping in the S component and to a small extent glycoproteins B and C mapping in the L component. A variety of studies have suggested that the strongest neutralizing antibody is induced by glycoprotein D. This glycoprotein, even by itself, induces some protection in experimental animal systems. The glycoproteins G, D, and E map in close vicinity to each other in the S component of HSV DNA.

To enable a recombinant virus to confer protection against both HSV-1 and HSV-2, a fragment of HSV-2 DNA carrying glycoproteins D and G genes was inserted into a recombinant virus according to the invention. This recombinant was constructed from recombinant I358 by removal of the unique sequences from the L component, the TK gene, and the HindIII O sequences from the I358 genome.

A desirable property of potential HSV vaccines is that they should not contain transforming domains. Transforming domains are defined as those which confer upon recipient cells the ability to become morphologically transformed and to establish tumors on transplantation in experimental animals. All of the transforming regions in HSV-2 genome are mapped in the L component of HSV-2 DNA. The corresponding sequences of HSV-1 genome do not immortalize or confer malignant transforming properties to cells. The DNA fragment carrying the genes for glycoprotein D and G does not contain sequences known to be able to transform cells in culture.

Extensive literature exists to the effect that TK$^-$ viruses (i.e. viruses lacking a TK gene) have a reduced capacity to establish latent infections in experimental animals. The parent virus of I358 (designated $\Delta$305, described in Poffenberger et al (1983), and Poffenberger and Roizman (1985), cited above) does not establish latency in experimental animals and it is thus reasonable to expect that the derivatives of I358 lacking the TK gene would also fail to establish latency.

The question existed prior to the invention, however, whether TK$^-$ viruses, although having reduced capacity to establish latency, would confer protection. Therefore, recombinants R7017 (ATCC VR2121) and R7020 (ATCC VR2123) have been constructed according to the invention. Both viral genomes contain a deletion of approximately 500 bp within the domain of the TK gene between and including the BglII and SacI sites thereof. However, in the case of R7020, a TK gene was inserted, not at its natural location but at a novel junction between the L and S components. The rationale here was to void the possibility that restoration of the TK gene at its natural site may increase the virulence of the recombinant. The results of tests show that both recombinants are capable of conferring protection against challenge by wild type virus and were attenuated with respect to neurovirulence in mice.

If desired, a foreign gene (other than and in addition to the HSV-2 glycoprotein gene) may be inserted into the recombinant genome and expressed according to the procedure disclosed in copending, commonly assigned U.S. patent application Ser. No. 616,930 filed June 4, 1984 in the name of Bernard Roizman. The entire disclosures of U.S. application Ser. No. 616,930 and its European Patent Office counterpart, Publication No. 176,170 published Apr. 2, 1986, are incorporated herein by reference.

PROCEDURE FOR CONSTRUCTING RECOMBINANT VIRUSES

According to the invention, recombinant herpes simplex viruses, each having a genome which is a mutant of the HSV-1 genome, and which are effective as vaccines against both virulent HSV-1 and HSV-2, and which also may act as vectors of foreign genes, have been prepared.

In the recombinant genome, the portion thereof which is responsible for neurovirulence yet non-essential for growth and which is located at or near the internal inverted repeated sequences of the HSV-1 genome in the prototype arrangement is deleted. Specifically, it has been found that deletion from the HSV-1 genome of all sequences between the 3' terminus of the $\alpha$27 gene and the promoter region of the $\alpha$4 gene is sufficient to attenuate the genome without inhibiting its ability to grow, while providing sufficient space for the insertion of genetic material without affecting the packaging of the genome.

Following the above-identified deletion, a gene from the genome of HSV-2 which is responsible for coding one or more immunity-inducing glycoproteins (e.g. glycoproteins B, C or D) of HSV-2 is inserted in the mutant genome between the end points of deletion.

Preferably, the gene coding for HSV-2 glycoprotein D is inserted. This gene may be associated with all or part of adjacent genes which code HSV-2 glycoprotein G and E.

Following the foregoing deletion and insertion steps, the resulting mutant genome is cotransfected with the genome of parenteral HSV-1 under conditions permitting recombination at sites of DNA sequence homology to produce recombinant progeny. The progeny are then selected for recombinant genomes lacking the deleted portion of the parenteral genome, and the selected genomes are screened for the presence of the inserted HSV-2 glycoprotein coding gene.

In general, the deleted portion of the HSV-1 genome (e.g. about 500 base pairs between and including the BglII and SacI sites of the thymidine kinase gene) will render the thymidine kinase gene incapable of expressing a functional enzyme. In one form of the recombinant genome, a thymidine kinase gene is inserted into the mutant genome at other than its natural location under the regulation of a promoter, such as the promoter region of the $\alpha$4 gene of the HSV-1 genome. (The thymidine kinase gene may be from either a HSV-1 or HSV-2 genome.) Promoter fusions have been described in the literature. See, for example, Post et al, *Cell*, Vol. 24 at 555–565 (1981).

Details of the laboratory procedures used to prepare two exemplary recombinant viruses (R7017 and R7020) of the invention follow. Throughout, cloning was carried out using standard laboratory procedures such as described in detail in Maniatis et al., *Molecular Cloning-A Laboratory Manual*, Cold Spring Harbor Laboratory (1982). U.S. Pat. No. 4,769,331 issued Sept. 6, 1988 in the names of Roizman and Post, and its counterpart European Patent Publication No. 74,808 (Mar. 23, 1983), the respective disclosures of which are incorporated hereby by reference, disclose a procedure for insertion, deletion and substitution of DNA sequences which is useful in the present invention.

Plasmids and virus strains not identified by ATCC accession number (as well as some identified by ATCC accession number) are not critical to the disclosed procedure, but were selected for convenience, as HSV fragment libraries are widely available and are well known in the art. See, for example, Post et al, *Proc. Natl. Acad. Sci. USA*, Vol. 77, No. 7 at 4201–4205 (1980).

The wild-type parent viruses used herein were HSV-1 strain F [HSV-1(F)] (ATCC VR 733) and HSV-2 strain G [HSV-2(G)] (ATCC VR 734). Fragment libraries were made from the respective genomes of these two viruses by standard techniques.

Recombinant R7017 was constructed from recombinant I358, identified above. The objective was to remove from the I358 DNA all of the sequences located between the terminus of the $\alpha$27 gene and the promoter region of the $\alpha$4 gene. In the case of the wild type virus, this includes the following:

(a) unidentified genes located between the $\alpha$27 gene and the $\alpha$0 gene;

(b) one copy of the α0 gene located in the internal inverted repeats;

(c) one copy of the γ₁34.5 gene located between the α0 gene and one or more a sequences forming the natural junction between the L and S components;

(d) all a sequences and one copy of the sequences designated as C' and located between the a sequence and the 3' terminus of the α4 gene; and (e) all of the coding sequences of the α4 gene and the copy of the 5' transcribed non-coding sequences and of the α4 gene located in the internal inverted repeats up to the BamHI cleavage site between BamHI Y and BamHI N fragments.

In the case of I358 DNA, some of these sequences were already missing. Additional sequences to be removed were as follows:

(a) an unidentified number of sequences between the terminus of the α27 gene and the left terminus of the α0 gene;

(b) a portion of the HindIII 0 fragment reiterated in the I358 genome and responsible for generation of defective genomes as reported by Poffenberger and Roizman (1985), cited above; and, (c) the TK gene located adjacent the sequences from HindIII 0 fragment.

In order to make the desired deletions, a plasmid designated pRB3410 (ATCC 53350) was constructed. The plasmid pRB3410 contains a polylinker into which was inserted the α27 gene and the promoter of the α4 gene to serve as flanking sequences for recombination. The polylinker also contained convenient restriction endonuclease sites for insertion of genes between the flanking sequences. In the case of recombinant R7017, the HindIII L fragment containing the glycoprotein genes D and G of HSV-2 virus was inserted into the polylinker sequences.

Recombinant R7020 differs from recombinant R7017 in that it contains the structural sequences and 5' transcribed non-coding sequences of the TK gene sandwiched between the inserted HindIII L fragment and the α4 promoter. The TK gene is regulated by the α4 promoter.

CONSTRUCTION OF RECOMBINANT R7017

Figure 1:
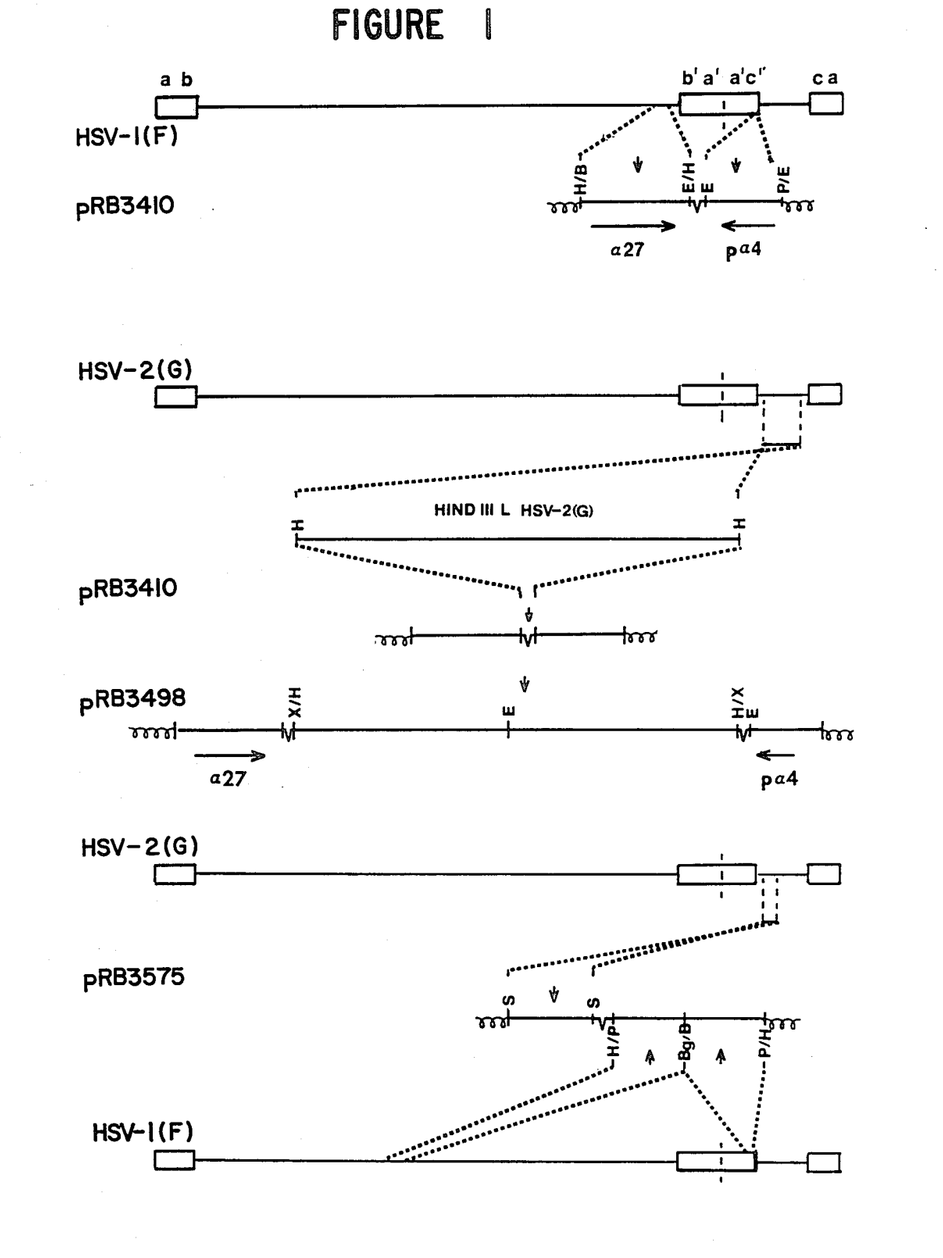
FIG. 1 is a schematic diagram of the construction of plasmids pRB3410, pRB3498, and pRB3575 used in constructing exemplary recombinant virus strains of the invention. The upper line represents the sequence arrangement of HSV-1 DNA. The boxes represent inverted repeat sequences ab, b'a'c', and ca. HSV-2 has a similar structure.

Plasmid pRB3410 was constructed in two steps as shown schematically in FIG. 1. First, the 2.4 Kbp BamHI-SacI fragment from BamHI B contained in plasmid pRB404 was inserted as a BamHI-EcoRI fragment from pRB404 into the HindIII site of plasmid pUC13 by T4 polymerase treatment. [Plasmid pRB404 is a convenient, routine source of the intact α17 gene, and carries the α27 gene in the form of a small BamHI-SalI fragment from the BamHI B fragment of HSV-1. It was prepared by digestion of BamHI B with SalI, treated with polymerase and cloned in pRB1 (a derivative of pBR322, ATCC 31344) as an EcoRI fragment (pRB1 is pBR322 with the SalI site removed by nuclease digestion). Plasmid pUC13 is well known and is commercially available from Pharmacia, Inc., Piscataway, N.J., U.S.A.]

Then, the 1.8 Kbp EcoRI-PvuII fragment from the BamHI N fragment of HSV-1 (F) contained in plasmid pRB403 (ATCC 39719) was inserted into the EcoRI site of pUC13, also after T4 polymerase treatment. (Plasmid pRB403 carries the left end of BamHI cloned as BamHI-PvuII fragment in pBR322. This is a convenient source of the α4 gene promoter since it is smaller than the entire BamHI N fragment.) The 2.4 KB BamHI-SacI fragment contains the entire α27 gene including its own promoter whereas the EcoRI-PvuII fragment contains only the promoter for the α4 gene. See Post et al (1981), cited above, and Kristie et al, *Proc. Natl. Acad. Sci. USA*, Vol. 81 at 4065-4069 (1984). In the wild type genome, the two fragments are separated by approximately 8 KB of BamHI B, and the entire BamHI S, BamHI P, and BamHI Y fragments within the internal inverted repeats of the S component.

Plasmid pRB3410 was constructed so as to contain a polylinker with unique restriction endonuclease cleavage sites between the α27 gene and the α4 promoter so that additional DNA sequences could be inserted into sites and placed within the viral genome of I358 using the flanking homology provided by the α27 gene and the α4 promoter. Into the Xba I site of the polylinker in pRB3410 was inserted the 9.5 Kbp HindIII L fragment of HSV-2(G) after polymerase treatment. This fragment was purified from agarose after electrophoresis of the HindIII digest of plasmid pRB804 containing the HindIII L fragment of HSV-2(G) cloned into the HindIII site of plasmid pACYC177 (ATCC 37031). [Plasmid pRB804 is a clone of the HindIII L fragment of HSV-2 cloned into the HindIII site of pACYC 177. It contains the intact coding regions of gG, gD and a portion of the coding sequence of gE of HSV-2. Plasmid pACYC177 is widely available and can be substituted for by plasmid pBR322, if desired. See Chang et al, *J. Bacteriol.*, Vol. 134 at 1141 (1978)]. The fragments from pRB403 and pRB404 provided flanking homologous sequences for the various recombination events to follow.

Figure 2:
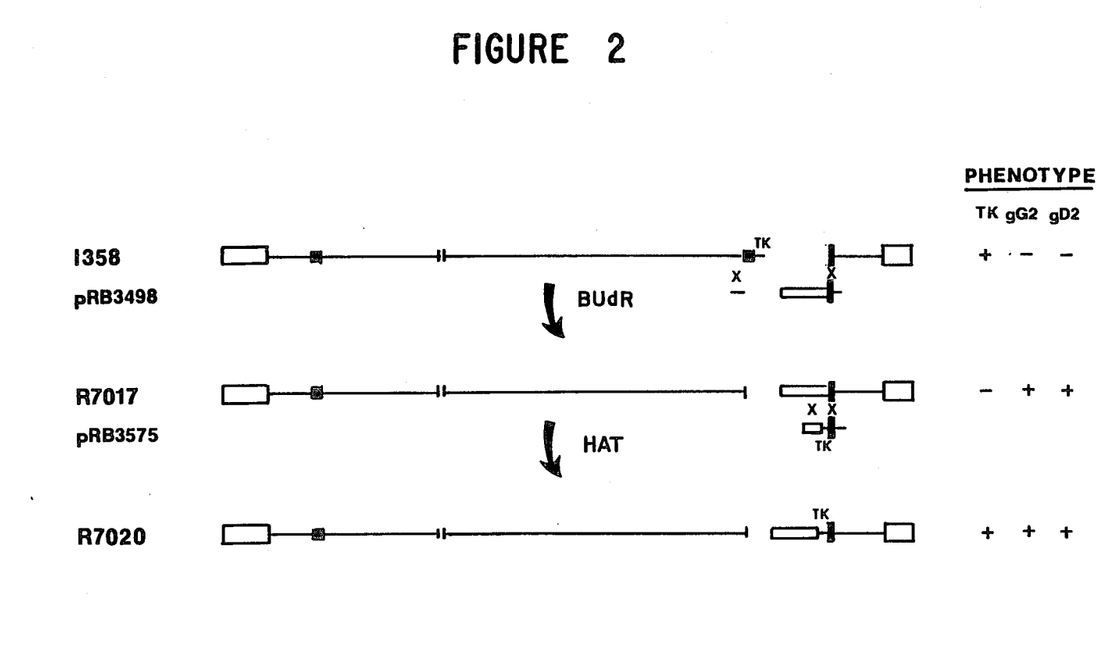
FIG. 2 is a series of schematic diagrams demonstrating the steps in the construction of exemplary recombinant virus strains R7017 and R7020 of the invention.
Figure 3:
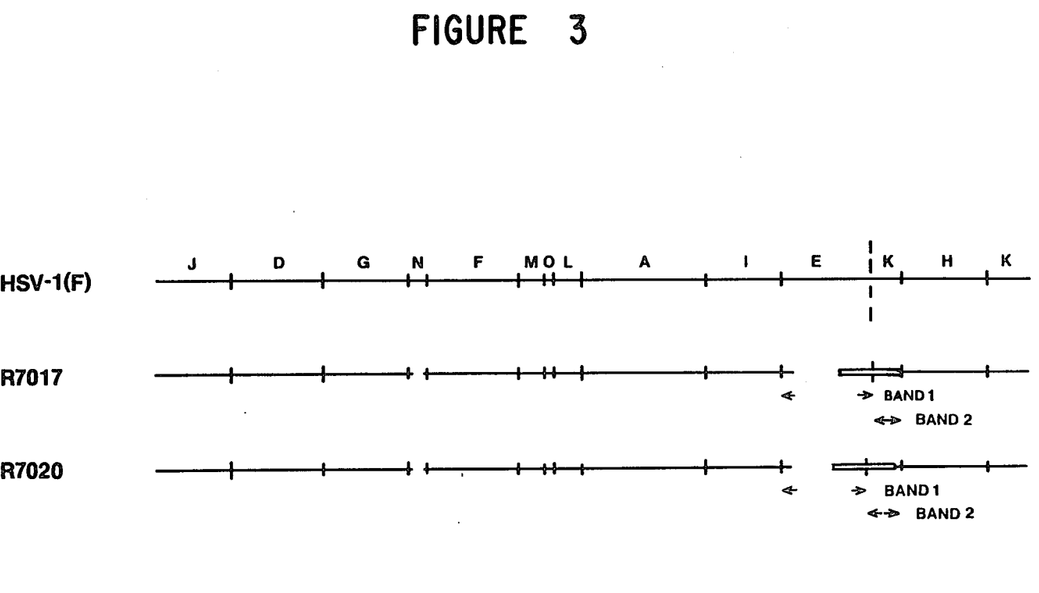
FIG. 3 is a series of schematic diagrams illustrating the sequence arrangements of the recombinant viral strains R7017 and R7020 of FIG. 2. The interruption in the EcoRI N fragment is intended to indicate the site of the deletion in the thymidine kinase gene. The new bands at the novel junction between the L and S components are designated as Bands 1 and 2, respectively.
Figure 4A:
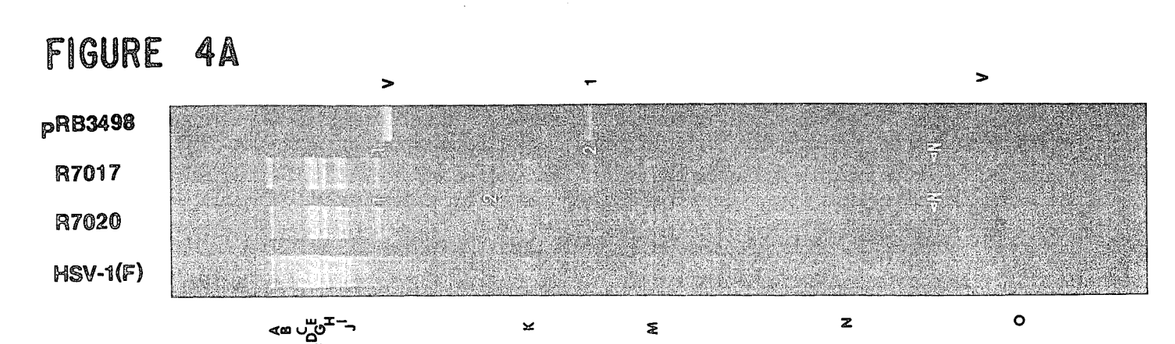
FIG. 4A is a photomicrograph of EcoRI restriction endonuclease maps of the respective genomes of a wild type HSV-1 virus, recombinant virus strains R7017 and R7020 of FIGS. 2 and 3, and plasmid pRB3498.
Figure 4B:
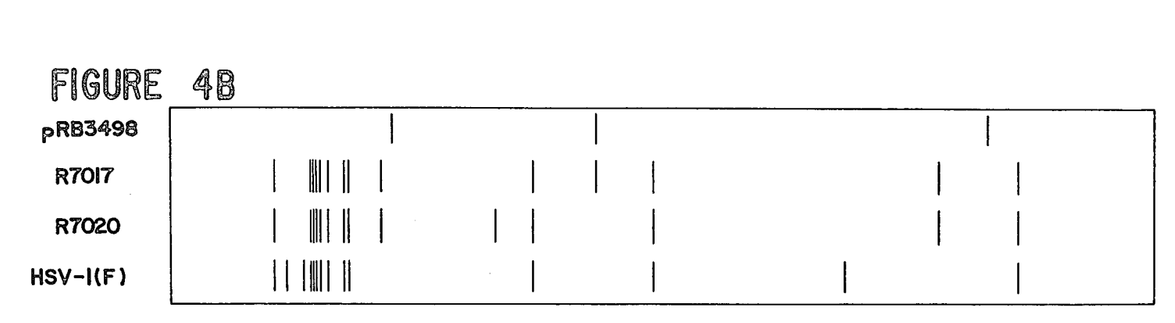
FIG. 4B is a pen and ink depiction of the bands of FIG. 4A.

The resulting recombinant plasmid pRB3498 (ATCC 53348) was cotransfected with intact I358 DNA into rabbit skin cells (see FIG. 2). The progeny of the transfection were plated onto 143TK⁻ cells in the presence of medium containing a mixture of 199-V supplemented with 3% fetal bovine serum and bromouracildeoxyriboside (BUdR). The I358 progeny were destroyed by BUdR since the virus is TK⁺. The TK⁻ recombinant virus (designated R7017) that grew in the presence of BUdR was plaque purified and tested by restriction endonuclease analysis for predicted structure (FIGS. 3 and 4) and by the biotin-avidin enhanced surface immunoassays (Kousoulas et al., *Virology*, Vol. 135, pp. 379-395, 1984) with HSV-2(G) specific monoclonal antibody H966 to glycoprotein G (Roizman, et al., *Virology*, Vol. 133, pp. 242-247, 1984) for the presence of the HSV-2(G) glycoprotein G gene. See Table 1, below.

Recombinant virus R7017 corresponds to a recombinant virus R3410 (ATCC VR2124) but containing the HSV-2 HindIII L fragment. The R3410 virus could be prepared by cotransfecting I358 with plasmid pRB3410 or, alternatively, I358 can be cotransfected with pRB3410 containing the inserted HSV-2 HindIII L fragment to yield a derivative of recombinant R3410 additionally containing the HSV-2 L fragment. The latter recombinant virus is designated R7017.

CONSTRUCTION OF RECOMBINANT R7020

The 1.8 Kbp SacI-HindIII fragment from the HSV-2(G) HindIII L fragment closest to the α4 promoter in the R7017 viral genome was cloned as a SacI fragment from pRB3498 into the SacI site of plasmid pUC18 (ATCC 37353). (pUC18 is commercially available from Pharmacia, Inc. Piscataway, N.J., U.S.A.). An α4 regulated TK gene was cleaved as a PvuII fragment from plasmid pRB316 (Post et al, 1981, cited above) and cloned into the HindIII site of plasmid pRB3498 by T4 polymerase to yield plasmid pRB3575 (ATCC 53349) (FIG. 1). (Plasmid pRB316 is a convenient source of α-regulated TK gene. This plasmid carries HSV-1 BamHI N fused to the larger BamHI-BglII fragment of BamHI Q cloned in pBR 322. In this fusion, the promoter of the α4 gene is fused to the 5' transcribed coding and noncoding sequences of the TK gene such that the resulting chimeric gene is regulated as an α rather than a β gene.)

Plasmid pRB3575 was constructed so that there would be multiple cloning sites for the insertion of additional sequences between the regions of flanking homology with the R7017 viral genome. The recombinant plasmid pRB3575 was cotransfected with R7017 viral DNA and the resulting TK+ R7020 recombinant was isolated on the basis of its ability to grow in 143TK− cells in the presence of HAT medium (See FIGS. 2 and 3). The recombinant was verified by DNA restriction analysis, using EcoRI (FIGS. 3 and 4), and plaqued purified four times. The recombinants R7017 and R7020 were tested with various monoclonal antibodies as shown in Table 1.

TABLE 1

Reactivity of Viruses with Monoclonal Antibodies

| Antibody | HSV-1(F) | HSV-2(G) | R7017 | R7020 | Glycoprotein |
|---|---|---|---|---|---|
| 600 | + | − | + | + | gE-1 |
| H966 | − | + | + | + | gG-2 |
| H1301 | + | + | + | + | gE-1,2 |
| H1379 | + | − | + | + | gG-1 |
| H1380 | + | − | + | + | gD-1 |

EXAMPLES

The following specific examples are given in order to demonstrate the infectivity, ability to establish latency, immunogenicity, and lack of virulence of the two exemplary recombinant viruses of the invention. Another example demonstrates the comparative virulence of one of the exemplary recombinant viruses before and after serial passages in mouse brain.

EXAMPLE 1—INFECTIVITY OF VIRUSES R7017 AND R7020 BY EYE ROUTE IN MICE

Six week old Balb/c/Cenlco mice (IFFA-Credo, Les Oncins, France) were inoculated in both eyes with virus R7017 or R7020 under pentobarbitone anaesthesia. The cornea was scarified with 10 light strokes with a hypodermic needle and bathed with 10 ul of virus suspension. The eyelids were closed and gently massaged.

Two hours later, the mice were anaesthetized again and the eyes were washed with 50 ul of a solution of 16% human standard immunoglobulins (Institut Merieux, Lyon, France) diluted 1/10 in physiological saline solution. Immunoglobulin solution was flushed on and aspirated from the eye five times. The excess fluid was discarded leaving approximately 10 ul on the eye. The purpose of the immunoglobulin solution was to neutralize the virus that did not penetrate into the cornea.

Specimens for virus assay were collected on days 1, 2, 3, 4 and 7, immediately after exsanguination of the mice under anaesthesia. Tear film was sampled by washing the eye with phosphate buffer solution supplemented with glucose and inactivated calf serum (PBS Glu SVI). Approximately 50 ul were flushed on and aspirated from the eye five times and transferred in 1 ml of PBS Glu SVI. Trigeminal ganglia were aseptically removed after appropriate dissection and transferred in 1 ml of PBS Glu SVI, homogenized and submitted to three cycles of freezing and thawing.

All specimens were kept in ice bath and processed within one hour after sacrifice of the mice.

0.5 ml of tear film dilution or of ganglionic tissue suspension were plated on 25 $cm^2$ of Vero cell layer and allowed to absorb for one hour at 37° C. on a rotatory shaker. Inoculum was discarded and the cell layer fed with 5 ml of 199 medium supplemented with 1% of calf serum and a mixture of polymyxin and nystatin.

Cultures were examined daily for typical HSV cytopathic effect for 7 days. In positive cultures, the number of cytopathic foci was estimated and scored on the two first days of development of the plaques.

Results are shown in Tables 2 and 3, below.

TABLE 2

Infectivity of Viruses R7017 and R7020 by Eye Route in Mice[c]

| | R7017[a] $10^{6.3}$ pfu/eye | | R7020[b] ($10^{7.2}$ pfu/eye) | |
|---|---|---|---|---|
| Day | Tear Film | Trigeminal Ganglia | Tear Film | Trigeminal Ganglia |
| 1 | 6/6 | 0/6 | 6/6 | 1/6 |
| 2 | 5/6 | 0/6 | 5/6 | 0/6 |
| 3 | 3/6 | 0/6 | 5/6 | 0/6 |
| 4 | 3/6 | 0/6 | 5/6 | 1/6 |
| 7 | 1/6 | 0/6 | 0/6 | 0/6 |

[a]Test no. 46
[b]Test no. 45
[c]All results are given as number of positive specimens/number specimens tested

TABLE 3

Infectivity of Viruses R7017 and R7020 by Eye Route in Mice

| Virus[c] | R7017[a] | | | R7020[b] | | |
|---|---|---|---|---|---|---|
| Recovery | <10 | 10-100 | 101-1000 | <10 | 10-100 | 101-1000 |
| Day 1 | 2 | 3 | 1 | — | 6 | — |
| Day 2 | 3 | 2 | — | 1 | 4 | — |
| Day 3 | 3 | — | — | 4 | 1 | — |
| Day 4 | 3 | — | — | 3 | 2 | — |
| Day 7 | 1 | — | — | — | — | — |

[a]Test no. 46
[b]Test no. 45
[c]Number of cytopathic foci on isolation plates

Table 2 shows the number of mice of the total assayed from which virus could be isolated in the tear film and in the trigeminal ganglion. The data indicate that both viruses multiplied as evidenced by their presence in the tear film. However, only R7020 was able to establish infections of the ganglia as shown in Table 2. Table 3 shows that the number of cytopathic foci, which reflects the amounts of virus in the tear film, were approximately similar, i.e. that both viruses were capable of multiplying at the site of inoculation.

EXAMPLE 2—VIRULENCE OF VIRUSES R7017 AND R7020 BY INTRACEREBRAL ROUTE IN MICE

Six week old male Balb/c/Cenlco mice were obtained from IFFA-Credo (Les Oncins, France). Groups of 20 mice were injected intracranially with virus R7017 or R7020 under pentobarbitone anaesthesia with 50 ul of serial ten fold dilutions of virus suspensions. For R7017, the virus titer was 8.4 (log pfu/ml). The titer for R7020 was 9.3 (log pfu/ml).

To increase the maximum dose of virus per mouse as well as to reduce interferences caused by additives, viruses used in this experiment were aliquots of lots 95 and 96 (viruses R7020 and R7017 respectively) prepared and stored without skim milk.

Mice were observed daily for 3 weeks after inoculation. Lethal doses were calculated from the mortality pattern according the 2 arc sinus method. For each of R7017 and R7020, the calculated lethal dose (LD$_{50}$) was $10^{6.43}$ pfu/mouse.

Figure 5:
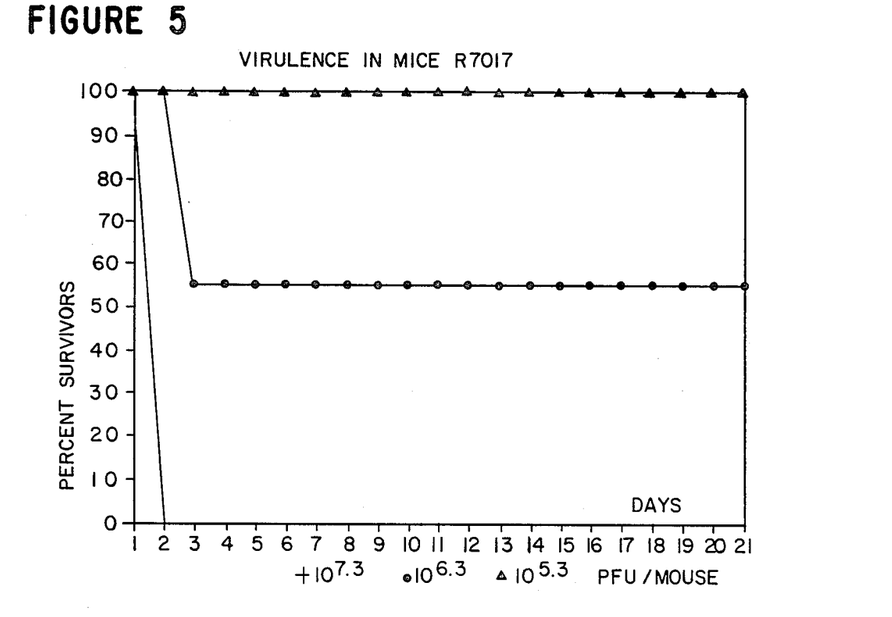
FIGS. 5 and 6 are graphical representations depicting the virulence in mice of recombinant strains R7017 and R7020, respectively, at various dosages, as described in detail in Example 2.
Figure 6:
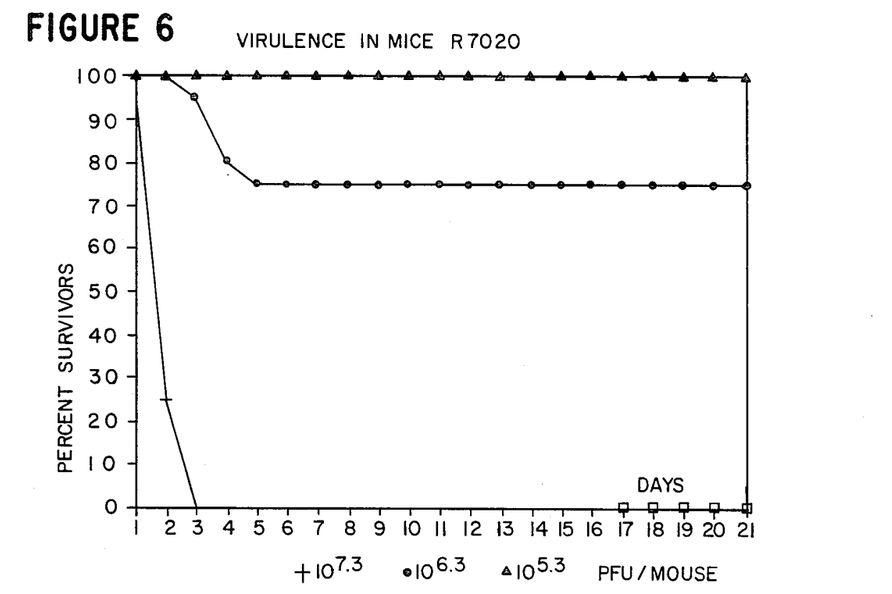
Figure 7:
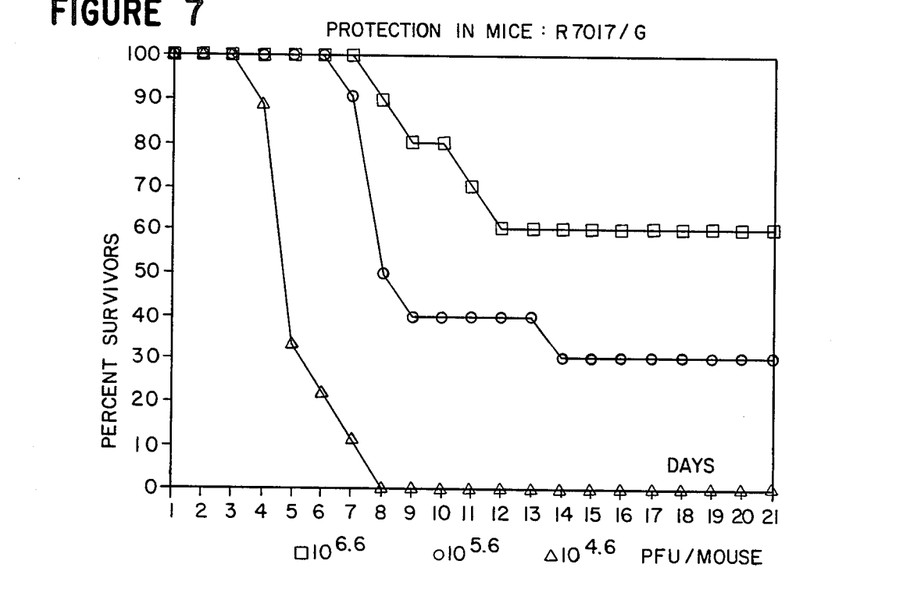
FIGS. 7 and 8 are graphical representations depicting protection in mice against challenge by HSV conferred by inoculation with recombinant virus R7017, at various protective dosages, as described in detail in Example 3.
Figure 8:
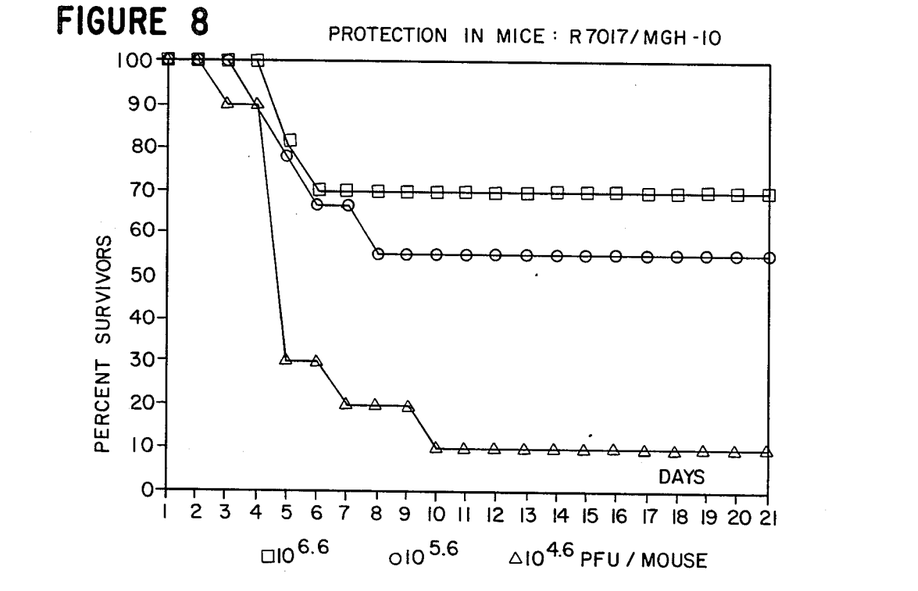
Figure 9:
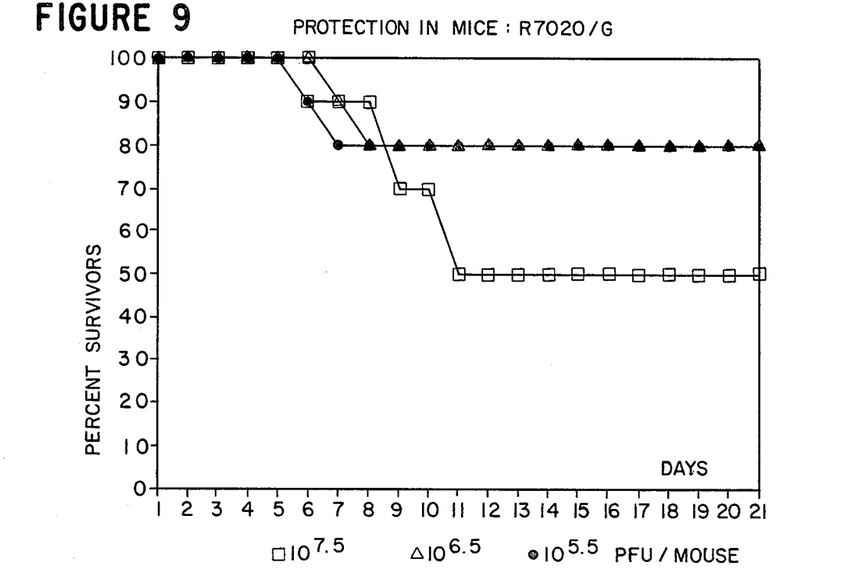
FIGS. 9 and 10 are graphical representations depicting protection in mice against challenge by HSV conferred by inoculation with recombinant virus R7020, at various dosages, as described in detail in Example 3.
Figure 10:
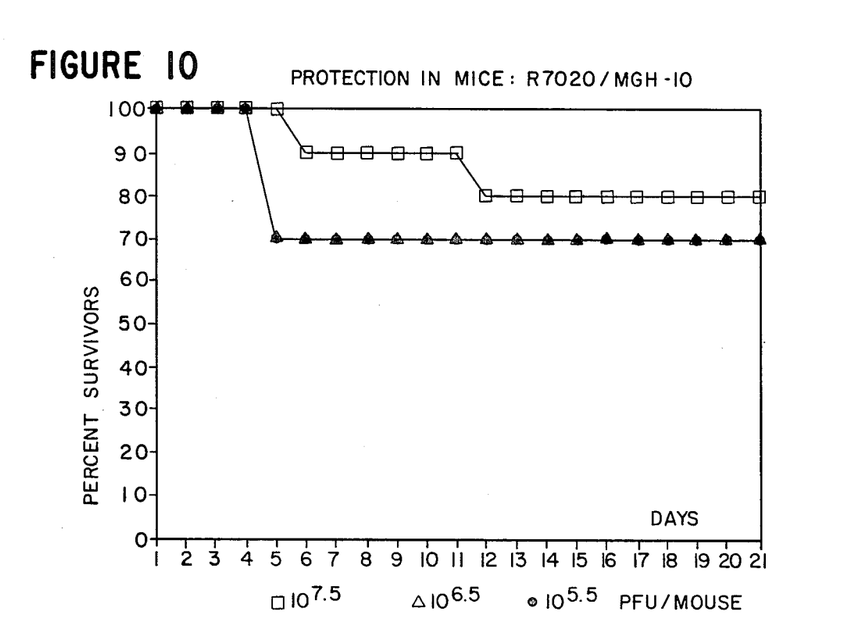
Figure 11:
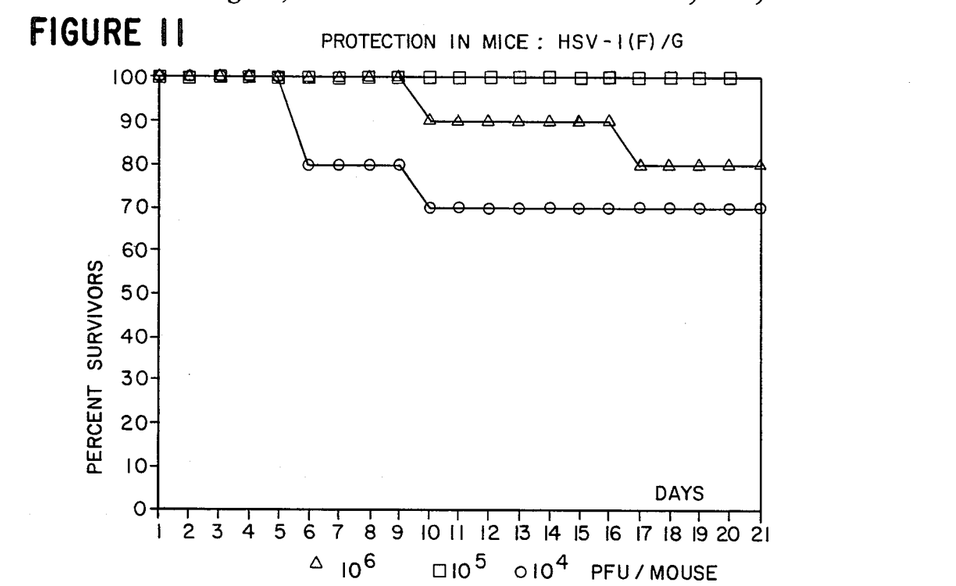
FIGS. 11 and 12 are graphical representations of protection in mice against challenge by HSV conferred by inoculation with HSV-1(F), at various dosages, as described in Example 3.
Figure 12:
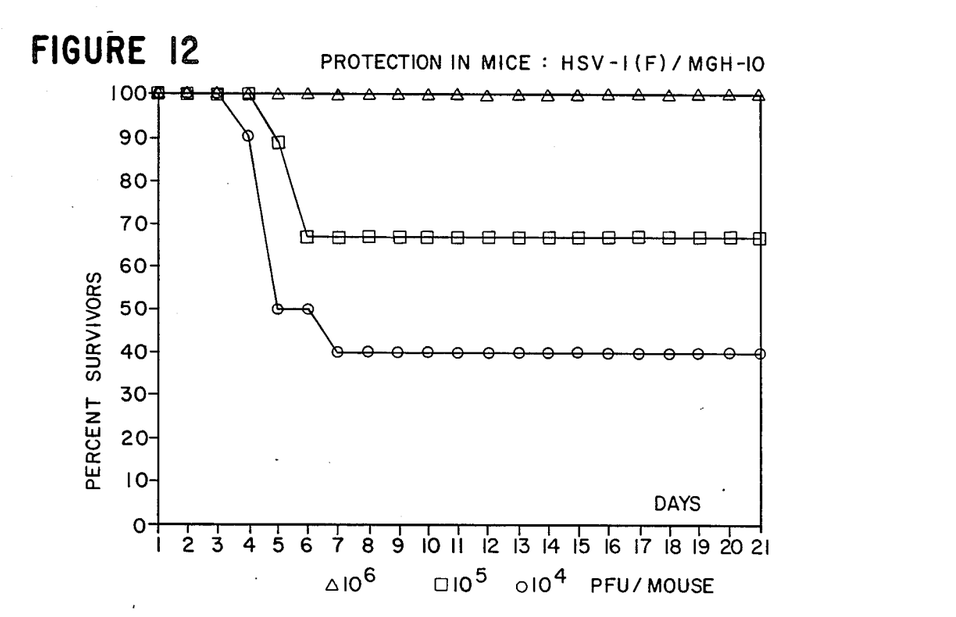

The results are depicted graphically in FIGS. 5 and 6.

The foregoing indicates that both viruses are relatively attenuated since the lethal dose 50% (LD$_{50}$) for the parent virus [HSV-1(F)] is $10^{1.5}$ pfu/mouse. In simple terms, the attenuated viruses are 100,000 times less virulent than the wild type viruses.

The results also indicate that the two recombinants did not differ with respect to the degree of attenuation as measured by intracerebral inoculation in mice.

EXAMPLE 3—IMMUNOGENICITY OF VIRUSES R7017 AND R7020 BY SUBCUTANEOUS ROUTE IN MICE

Six week old male mice [OF 1 (IOPS Caw)] were obtained from IFFA Credo (Les Oncins, France).

Groups of 20 mice were injected in the right foot pad with 20 ul of serial ten fold dilutions of virus suspensions. Viruses used included R7017 and R7020 as well as HSV-1(F) as a control.

To increase the maximum dose of virus per mouse as well as to reduce interferences caused by additives, viruses R7017 and R7020 used in this experiment were aliquots of lots 96 and 95 respectively, prepared and stored without skim milk.

Mice were challenged 4 weeks later by intracerebral route under pentobarbitone anaesthesia with 50 ul containing 300 lethal doses of either HSV-1 (MGH 10) or HSV-2 (G).

The mice were observed daily for 3 weeks after challenge. Protective doses were calculated from the survival pattern according to the 2 arc sinus $\sqrt{p}$ method.

Results are shown in Table 4, below, and are depicted graphically in FIGS. 7–12.

TABLE 4

| Immunogenicity of Virus R7017 and R7020 in Mice[a] | | |
|---|---|---|
| Immunizing | Challenge Virus | |
| Virus | MGH 10 | G |
| R7017 | $10^{5.80}$ | $10^{6.27}$ |
| R7020 | $<10^{5.5(b)}$ | $<10^{5.5(b)}$ |
| HSV-1(F) | $10^{4.28}$ | $<10^{4(b)}$ |

[a]Protective doses 50% in pfu/mouse
[b]Estimated values

These studies indicate that the attenuated recombinant viruses were able to protect mice from lethal doses of challenge virus [HSV-1 (MGH 10) and HSV-2 (G)]. The protection is not as good as that afforded by wild type virus (by a factor of 10 to 50) and therefore the recombinants have to be used in 10- to 50-fold higher concentrations than wild type viruses to give the same protection. However, the recombinants have a much greater safety margin and, as shown in Example 2, are 100,000-fold less virulent than the wild type viruses.

EXAMPLE 4—ABILITY TO ESTABLISH LATENCY

Six week old Balb/c/Cenlco mice (IFFA-Credo, Les Oncins, France) were inoculated with virus R7017 and R7020 in the right eye under pentobarbitone anaesthesia. The cornea was scarified with ten light strokes with a hypodermic needle and bathed with 10 ul of undiluted stock virus suspension. The eyelids were closed and gently massaged.

Four weeks later, mice were anaesthetized and exsanguinated. Right trigeminal ganglia were immediately removed and incubated for 4 or 5 days in maintenance medium (199V) at 37° C. under air-CO$_2$ atmosphere (96:4 v/v).

Ganglia were then homogenized in a tissue grinder. To assay for the presence of virus, the resulting suspension was transferred on Vero cells (25 cm$^2$ plastic flasks). After one hour absorption at 37° C. on a rotatory shaker, the inoculum was removed, maintenance medium was added and the flasks were incubated at 37° C.

Cultures were examined daily for seven days for cytopathic effects (CPE) characteristic of HSV infected cells. To improve the sensitivity of the detection, cultures not showing HSV CPE were frozen and thawed once at the end of the examination period and the cell suspension was assayed for HSV as set forth above.

The results are shown in Table 5, below.

TABLE 5

| | Ability to Establish Latency | |
|---|---|---|
| Virus | Inoculum (pfu/eye) | Mice Yielding Latent Virus/Mice Tested |
| R7017 | $10^{6.3}$ | 0/20 |
| R7020 | $10^{7.2}$ | 1/20 |

The results indicate that R7020 is potentially capable of establishing latency in mice even though the levels were low (1 mouse in 20). The results with R7017 were consistent with those of reports that TK$^-$ viruses are generally not capable of establishing latency or are grossly affected in their ability to do so.

EXAMPLE 5—SERIAL PASSAGES OF VIRUS R7020 IN MOUSE BRAIN

Six week old male mice [ICO: OF1 (IOPS Caw)] were obtained from IFFA-Credo, Les Oncins, France. Groups of 8 mice were injected by intracerebral route under pentobarbitone anaesthesia with approximately $10^6$ plaque forming units (pfu) of virus R7017 and R7020 in 50 ul.

Three days later (occasionally 2 days), 3 mice were randomly drawn and sacrificed. Each brain was aseptically removed and transferred in 4.5 ml of phosphate buffer saline supplemented with glucose and inactivated calf serum (PBS Glu SVI). Tissues were homogenized and subjected to 3 cycles of freezing and thawing. Homogenates were then clarified by refrigerated centrifugation for 10 minutes at 900 g.

Supernatants were pooled and used for:
(i) infectivity titration by the plaque count method on Vero cells under liquid overlay supplemented with human immunoglobulins; and
(ii) preparation of virus stock on Vero cells.

1 ml of clarified suspension was plated on each of two 25 cm$^2$ cell layers and allowed to adsorb for one hour at room temperature on a rotatory shaker. Then, inoculum was discarded and replaced with 199 medium supplemented with 1% inactivated calf serum.

Cultures were incubated at 36° C. and examined daily. Progeny virus was harvested when 90 to 100% of the layer showed cytopathic effect. Cultures were frozen and thawed three times and the resulting suspension stored without addition of milk at −70° C. The stock was titered on Vero cells prior being injected as the next passage in mice.

Back titrations showed that multiplicity of infection ranged from 0.01 to 0.001.

Virulence titrations were carried out in groups of ten 6-week old male ICO OF1 mice (IFFA-Credo, Les Oncins, France). Fifty ul of serial tenfold dilutions of virus stocks were injected intracerebrally under pentobarbitone anaesthesia. Survival was monitored for three weeks after inoculation and lethal doses 50% ($LD_{50}$) were calculated from the mortality pattern by the 2 arc sin $\sqrt{p}$ method.

The viruses tested were: (1) an initial stock of virus R7020 (lot no. 95), containing $10^{9.17}$ pfu/ml (referred to as passage zero), and (ii) a stock made on Vero cells infected with a homogenate of 3 brains from mice innoculated at the 9th serial passage so that this virus underwent only one passage in cell culture after the last passage in mice. It titered $10^{9.90}$ pfu/ml (average of two titrations).

Results are shown in Table 6, below.

TABLE 6

| Passage 0 | | Passage 9 | |
|---|---|---|---|
| Inoculum log pfu/Mouse | Mice Dead/ Injected | Inoculum log pfu/Mouse | Mice Dead/ Injected |
| 4.87 | 0/10 | 5.60 | 1/10 |
| 5.87 | 2/10 | 6.60 | 9/10 |
| 6.87 | 10/10 | 7.60 | 10/10 |
| PBS Control | 0/10 | | 0/10 |
| pfu/$LD_{50}$ | $10^{6.04}$ | | $10^{6.22}$ |

In principle, deletions are permanent—they cannot be restored by mutation. However, mutations which may occur elsewhere in the genome are occasionally capable of restoring the deleted function in part.

This example demonstrates that serial passages in mouse brain did not result in the selection of virulent virus, and indicates that compensatory mutations did not occur.

The foregoing examples and disclosure illustrate that the recombinant virus strains of the invention exhibit the characteristics of immunogenicity, avirulence, lack of a tendency to revert to virulence and, in the case of virus R7017, the lack of persistence in the host following immunization. Further, the recombinant strains are effective in inducing immunity against both wild-type HSV-1 and HSV-2.

One particularly useful aspect of the recombinant viruses of the invention is the fact that ample space is available in the genomes thereof for the insertion of foreign genes such as to enable the use of the recombinants as vectors of these genes. For example, while virus I358 contains a deletion of about 13 KB, recombinant R3410 contains a deletion of about 15 KB. Recombinant R7017 retains about 8 KB available for insertion of foreign genes.

IMMUNIZATION ROUTES, DOSAGES AND INDICATIONS

A human host is preferably inoculated with a vaccine comprising an immunity inducing dose of one or more of the live vaccinal recombinant strains of the invention by the parenteral route, preferably by intramuscular or subcutaneous injection. Also, inoculation can be effected by surface scarification, or by inoculation of a body cavity. Typically, one or several inoculations of between about 10 and 1,000,000 pfu each, as measured in susceptible human or nonhuman primate cell lines, are sufficient to effect immunization of a human host.

Indications for vaccination include:

(a) a desire or need to boost the level of immunity of the host;

(b) a lack of immunity in the face of a high probability of natural infection; or (c) a lack of immunity and a likelihood that the subject will become immunologically compromised because of immunosuppressive therapy in the immediate or not too distant future.

The vaccine of the invention may be conveniently utilized in liquid form or in freeze-dried form, in the latter case in combination with one or more suitable preservative and protective agents to protect the vaccinal strains during the freeze drying process.

In addition to utility in immunizing a human host against wild-type HSV-1 and HSV-2, the recombinant strains of the invention are believed to have utility in treating a subject infected with wild-type HSV-1 and HSV-2. Treatment can be effected using similar dosages and routes of administration as used in immunization, described above.

The disclosures of all publications identified herein are expressly incorporated herein by reference.

The foregoing detailed description is given for clearness of understanding only, and no unnecessary limitations are to be understood or inferred therefrom, as modifications within the scope of the invention will be obvious to those skilled in the art.

I claim:

1. A recombinant herpes simplex virus (HSV), the genome of which comprises a mutant of the genome of HSV-1 wherein the portion of said HSV-1 genome which is responsible for neurovirulence yet non-essential for growth and which is located at or near the internal inverted repeated sequences of said HSV-1 genome is deleted, and wherein a portion of the genome of HSV-2 which is responsible for coding one or more immunity inducing portions of glycoproteins of said HSV-2 is inserted in said mutant genome between the end points of said deletion.

2. The recombinant virus of claim 1 wherein said deleted portion includes DNA sequences necessary for the function of the thymidine kinase gene of said HSV-1 genome.

3. The recombinant virus of claim 2 wherein about 500 base pairs between and including the BglII and SacI sites of said thymidine kinase gene are deleted.

4. The recombinant virus of claim 1 wherein all sequences of said HSV-1 genome between the 3' terminus of the α27 gene and the promoter region of the α4 gene are deleted.

5. The recombinant virus of claim 1 wherein said immunity inducing portion of glycoprotein is selected from the group consisting of glycoproteins B, C, and D of said HSV-2.

6. The recombinant virus of claim 5 wherein the portion responsible for coding for HSV-2 glycoprotein D is inserted in said mutant genome between said end points of deletion.

7. The recombinant virus of claim 6 wherein said portion coding for HSV-2 glycoprotein D is inserted as part of a DNA sequence containing all or part of the genes coding for HSV-2 glycoproteins G and E.

8. The recombinant virus of claim 1 wherein an HSV thymidine kinase gene is inserted into said mutant genome at other than its natural location under the regulation of a promoter.

9. The recombinant virus of claim 8 wherein said inserted HSV thymidine kinase gene is from an HSV-1 genome.

10. The recombinant virus of claim 8 wherein said promoter is the promoter of the α4 gene of said HSV-1 genome.

11. A recombinant herpes simplex virus (HSV), the genome of which comprises a mutant of the genome of HSV-1 wherein all sequences of said HSV-1 genome between the 3' terminus of the α27 gene and the promoter region of the α4 gene thereof are deleted, and wherein a portion of the genome of HSV-2 which is responsible for coding one or more of glycoproteins B, C and D of said HSV-2 is inserted in said mutant genome between the end points of said deletion.

12. The recombinant virus of claim 11 wherein said deleted portion includes DNA sequences necessary for the function of the thymidine kinase gene of said HSV-1 genome.

13. The recombinant virus of claim 12 wherein about 500 base pairs between and including the BglII and SacI sites of said thymidine kinase gene are deleted.

14. The recombinant virus of claim 11 wherein the portion responsible for coding for HSV-2 glycoprotein D is inserted in said mutant genome between said end points of deletion.

15. The recombinant virus of claim 14 wherein said portion coding for HSV-2 glycoprotein D is inserted as part of a DNA sequence containing all or part of the genes coding for HSV-2 glycoproteins G and E.

16. The recombinant virus of claim 11 wherein an HSV thymidine kinase gene is inserted into said mutant genome at other than its natural location under the regulation of a promoter.

17. The recombinant virus of claim 16 wherein said HSV thymidine kinase gene is from an HSV-1 genome.

18. The recombinant virus of claim 16 wherein said promoter is the promoter of the α4 gene of said HSV-1 genome.

19. Recombinant virus R7017 (ATCC VR2121)

20. Recombinant virus R7020 (ATCC VR2123).

21. A vaccine effective against both virulent HSV-1 and HSV-2 incorporating as an effective ingredient recombinant virus R7017 (ATCC VR2121).

22. A vaccine effective against both virulent HSV-1 and virulent HSV-2 incorporating as an effective ingredient recombinant virus R7020 (ATCC VR2123).

23. A method of immunizing a human host against virulent HSV-1 and virulent HSV-2, said method comprising the step of inoculating said host with an immunity-inducing dose of the vaccine of claim 21.

24. A method of immunizing a human host against virulent HSV-1 and virulent HSV-2, said method comprising the step of inoculating said host with an immunity-inducing dose of the vaccine of claim 22.

25. A method of preparing a recombinant herpes simplex virus (HSV) useful as an effective ingredient in a vaccine against both virulent HSV-1 and virulent HSV-2, said method comprising the steps of:
(a) deleting from the genome of parental HSV-1 the portion of said genome which is responsible for neurovirulence yet non-essential for growth and which is located at or near the internal inverted repeated sequences of said HSV-1 genome to provide a first mutant genome;
(b) inserting into said first mutant genome between the end points of said deletion of step (a) a portion of the genome of HSV-2 which is responsible for coding at least one immunity-inducing portion of glycoproteins of said HSV-2 to provide a second mutant genome;
(c) contransfecting said second mutant genome with the genome of said parental HSV-1 of (a) under conditions permitting recombination at sites of DNA sequence homology to produce recombinant progeny;
(d) selecting for a recombinant genome lacking the deleted portion of (a); and,
(e) screening said selected genome of (d) for the presence of said glycoprotein coding gene of (b).

26. The method of claim 25 wherein said deleted portion includes DNA sequences necessary for the function of the thymidine kinase gene of said parental HSV-1 genome.

27. The method of claim 26 wherein about 500 base pairs between and including the BglII and SacI sites of said thymidine kinase gene are deleted.

28. The method of claim 25 wherein all sequences of said HSV-1 genome between the 3' terminus of the α27 gene and the promoter region of the α4 gene are deleted.

29. The method of claim 25 wherein said immunity-inducing glycoprotein is selected from the group consisting of glycoproteins B, C and D of said HSV-2.

30. The method of claim 25 wherein the portion responsible for coding for HSV-2 glycoprotein D is inserted into said first mutant genome between said end points of deletion.

31. The method of claim 30 wherein said portion coding for HSV-2 glycoprotein D is inserted as a part of a DNA sequence comprising all or part of the genes coding for HSV-2 glycoproteins G and E.

32. The method of claim 29 wherein an HSV thymidine kinase gene is inserted into said first or second mutant genome at other than its natural location under the regulation of a promoter.

33. The method of claim 32 wherein said HSV thymidine kinase gene is from an HSV-1 genome.

34. The method of claim 32 wherein said promoter is the promoter of the α4 gene of said parental HSV-1 genome.

35. A method of preparing a recombinant herpes simplex virus (HSV) useful as an effective ingredient in a vaccine against both virulent HSV-1 and virulent HSV-2, said method comprising the steps of:
(a) deleting from the genome of parental HSV-1 all sequences of said HSV-1 genome between the 3' terminus of the α27 gene and the promoter region of the α4 gene thereof to provide a first mutant genome;
(b) inserting into said first mutant genome between the end points of said deletion of step (a) a portion of the genome of HSV-2 which is responsible for coding at least one immunity inducing portion of glycoproteins B, C and D of said HSV-2 to provide a second mutant genome;
(c) cotransfecting said second mutant genome with the genome of said parental HSV-1 of (a) under conditions permitting recombination at sites of DNA sequence homology to produce recombinant progeny;
(d) selecting for a recombinant genome lacking the deleted portion of (a); and, (e) screening said selected genome of (d) for the presence of said glycoprotein coding gene of (b).

36. The method of claim 35, wherein said deleted portion includes DNA sequences necessary for the function of the thymidine kinase gene of said parental HSV-1 genome.

37. The method of claim 36 wherein about 500 base pairs between and including the BglII and SacI sites of said thymidine kinase gene are deleted.

38. The method of claim 35 wherein the portion responsible for coding for HSV-2 glycoprotein D is inserted into said first mutant genome between said end points of deletion.

39. The method of claim 38 wherein said portion coding for HSV-2 glycoprotein D is inserted as part of a DNA sequence comprising all or part of the genes coding for HSV-2 glycoproteins G and E.

40. The method of claim 35 wherein an HSV thymidine kinase gene is inserted into said first or second mutant genome at other than its natural location under the regulation of a promoter.

41. The method of claim 40 wherein said HSV thymidine kinase gene is from an HSV-1 genome.

42. The method of claim 35 wherein said promoter is the promoter of the $\alpha 4$ gene of said parenteral HSV-1 genome.

43. Plasmid pRB3410 (ATCC 53350).

44. A recombinant herpes simplex virus (HSV), the genome of which comprises a mutant of the genome of HSV-1 wherein the portion of said HSV-1 genome which is responsible for neurovirulence yet non-essential for growth and which is located at or near the internal inverted repeated sequences of said HSV-1 genome is deleted, and wherein a portion of the HindIII L fragment of HSV-2 which is responsible for coding one or more immunity inducing portions of glycoproteins of said HSV-2 is inserted in said mutant genome between the end points of said deletion.

45. A vaccine effective against both virulent HSV-1 and virulent HSV-2 incorporating as an effective ingredient a recombinant herpes simplex virus according to any one of claims 1-10 and 44.

46. A method of immunizing a human host against virulent HSV-1 and virulent HSV-2, said method comprising the step of inoculating said host with an immunity-inducing dose of the vaccine of claim 45.

47. A recombinant herpes simplex virus (HSV), the genome of which comprises a mutant of the genome of HSV-1 wherein all sequences of said HSV-1 genome between the 3' terminus of the $\alpha 27$ gene and the promoter region of the $\alpha 4$ gene thereof are deleted, and wherein a portion of the HindIII L fragment of HSV-2 which is responsible for coding one or more of the glycoproteins of said HSV-2 is inserted in said mutant genome between the end points of said deletion.

48. A vaccine effective against both virulent HSV-1 and virulent HSV-2 incorporating as an effective ingredient an immunity inducing recombinant herpes simplex virus according to any one of claims 11-18 and 26.

49. A method of immunizing a human host against virulent HSV-1 and virulent HSV-2, said method comprising the step of inoculating said host with an immunity-inducing dose of the vaccine of claim 48.

50. A method of preparing a recombinant herpes simplex virus (HSV) useful as an effective ingredient in a vaccine against both virulent HSV-1 and virulent HSV-2, said method comprising the steps of:
  (a) deleting from the genome of parental HSV-1 the portion of said genome which is responsible for neurovirulence yet non-essential for growth and which is located at or near the internal inverted repeated sequences of said HSV-1 genome to provide a first mutant genome;
  (b) inserting into said first mutant genome between the end points of said deletion of step (a) a portion of the HindIII L fragment of HSV-2 which is responsible for coding at least one or more immunity-inducing portions of glycoproteins of said HSV-2 to provide a second mutant genome;
  (c) cotransfecting said second mutant genome with the genome of said parental HSV-1 of (a) under conditions permitting recombination at sites of DNA sequence homology to produce recombinant progeny;
  (d) selecting for a recombinant genome lacking the deleted portion of (a); and,
  (e) screening said selected genome of (d) for the presence of said glycoprotein coding gene of (b).

51. A method of preparing a recombinant herpes simplex virus (HSV) useful as an effective ingredient in a vaccine against both virulent HSV-1 and virulent HSV-2, said method comprising the steps of:
  (a) deleting from the genome of parental HSV-1 all sequences of said HSV-1 genome between the 3' terminus of the $\alpha 27$ gene and the promoter region of the $\alpha 4$ gene thereof to provide a first mutant genome;
  (b) inserting into said first mutant genome between the end points of said deletion of step (a) a portion of the HindIII L fragment of HSV-2 which is responsible for coding one or more of the glycoproteins of said HSV-2 to provide a second mutant genome;
  (c) cotransfecting said second mutant genome with the genome of said parental HSV-1 of (a) under conditions permitting recombination at sites of DNA sequence homology to produce recombinant progeny;
  (d) selecting for a recombinant genome lacking the deleted portion of (a); and,
  (e) screening said selected genome of (d) for the presence of said glycoprotein coding gene of (b).

* * * * *

UNITED STATES PATENT AND TRADEMARK OFFICE
CERTIFICATE OF CORRECTION

PATENT NO. : 4,859,587
DATED : August 22, 1989
INVENTOR(S) : Bernard Roizman

It is certified that error appears in the above-identified patent and that said Letters Patent is hereby corrected as shown below:

Column 7, lines 4, 6, and 7, delete "a" and insert --$\underline{a}$-- in lieu thereof.

Column 7, line 51 delete "$\alpha 17$" and insert --$\alpha 27$-- in lieu thereof.

Claim 42, at column 17, line 25 delete "parenteral" and insert --parental-- in lieu thereof.

Signed and Sealed this

Second Day of July, 1991

Attest:

HARRY F. MANBECK, JR.

Attesting Officer

Commissioner of Patents and Trademarks